(12) United States Patent
Samaras

(10) Patent No.: US 9,896,865 B2
(45) Date of Patent: Feb. 20, 2018

(54) METHOD AND APPARATUS FOR SANITIZING DOOR HANDLES

(76) Inventor: Gregory Samaras, Woodside, NY (US)

( * ) Notice: Subject to any disclaimer, the term of this patent is extended or adjusted under 35 U.S.C. 154(b) by 637 days.

(21) Appl. No.: 13/211,785

(22) Filed: Aug. 17, 2011

(65) Prior Publication Data

US 2012/0251387 A1 Oct. 4, 2012

Related U.S. Application Data

(60) Provisional application No. 61/470,686, filed on Apr. 1, 2010.

(51) Int. Cl.
*A61L 2/22* (2006.01)
*E05B 1/00* (2006.01)

(52) U.S. Cl.
CPC ............... *E05B 1/0069* (2013.01); *A61L 2/22* (2013.01)

(58) Field of Classification Search
CPC ........................................................ A61L 2/22
USPC ............................................................ 422/28
See application file for complete search history.

(56) References Cited

U.S. PATENT DOCUMENTS

| | | | |
|---|---|---|---|
| 1,491,780 A | 4/1924 | Abbott | |
| 1,783,097 A | 11/1930 | Polcari | |
| 2,527,955 A | 10/1950 | Pagel | |
| 5,314,668 A | 5/1994 | Biermaier | |
| 6,645,435 B2 | 11/2003 | Dawson et al. | |
| 6,874,697 B2 | 4/2005 | Calleung | |
| 7,360,674 B2 | 4/2008 | Sassoon | |
| 7,850,114 B2 | 12/2010 | Lavy | |
| 2004/0223894 A1* | 11/2004 | Gilbert | 422/292 |
| 2006/0153733 A1* | 7/2006 | Sassoon | 422/28 |
| 2008/0263820 A1 | 10/2008 | Blatz | |
| 2010/0003174 A1 | 1/2010 | Mohamed | |

FOREIGN PATENT DOCUMENTS

CA 2296152 A1 6/2000

* cited by examiner

*Primary Examiner* — Donald Spamer
(74) *Attorney, Agent, or Firm* — Schmeiser, Olsen & Watts, LLP

(57) ABSTRACT

The present invention is directed to a door handle sanitizing cassette that is installed within an internal cavity formed within a door. Prior to the installation, the cassette is fitted with all required door hardware and the equipment necessary to spray the door handles with a sanitizing liquid each time the door is opened or at preset intervals. The invention is designed to provide an inexpensive and easily installed system in public buildings to substantially reduce the spread of infectious disease by eliminating contaminated surfaces on the door handles.

12 Claims, 7 Drawing Sheets

METHOD AND APPARATUS FOR SANITIZING DOOR HANDLES

PRIORITY AND RELATED APPLICATIONS

This application claims priority to U.S. patent application Ser. No. 61/470,686 filed Apr. 1, 2011 entitled "HAND SANITIZER" which is hereby incorporated by reference in its entirety.

FIELD OF THE INVENTION

The present invention is directed to a method and apparatus for disinfecting door handles in order to prevent the spread of disease in healthcare facilities and other public and private structures.

BACKGROUND OF THE INVENTION

The transmission of disease by touching contaminated surfaces is well known, especially in healthcare associated facilities. Research studies have found the following key statistics relating to healthcare associated infections.

Infections developed during healthcare related treatment is the fourth leading cause of death in the United States and causes over 98,000 deaths per year which is more deaths than breast cancer, AIDS and automobile accidents combined. These infections add an average of $15,000 to a patient's bill and total over $40 billion a year in added healthcare costs.

A substantial number of the infections are caused by touching contaminated surfaces in a healthcare facility. Research has shown that only 38% of healthcare workers follow hand washing guide lines and nurses gloves were infected 42% of the time from touching surfaces in a patient's room. It has also been established that 80% of infectious diseases are transferred by touch, meaning person-to-person or surface-to-person. A study of 113 surfaces in hospital wards over a 14 day period showed that 76% of these surfaces had unacceptable levels of microbes after cleaning.

There are of course many surfaces in a healthcare environment that may be contaminated, but an extensive study in 2002 showed that 27% of door handles in a very large university hospital were contaminated with life threatening infections. As a large hospital would have thousands of door handles, it is clear that there is a significant chance of infection from door handles alone in a hospital environment. The chance of infectious disease from door handles is of course also applicable to non-healthcare facilities such as nursing homes, restaurants, movie theatres, malls, train and bus stations, fitness centers, schools and any other public facility.

There are a number of prior art patents directed to sanitizing door handles. Examples of such patents include U.S. Pat. No. 6,645,435 to Dawson et al, U.S. Pat. No. 6,879,697 to Callueng, U.S. Pat. No. 7,360,674 to Sassoon and U.S. Pat. No. 7,850,114 to Lavy. In general, the known prior art patents directed to sanitizing door handles describe devices that for the most part are mounted on the surface of the door or describe complex mechanisms or methods for sanitizing the door handle.

It is therefore an object of the present invention to provide an apparatus for sanitizing door handles that fits within the door and is compatible with most, if not all, of the doors typically used in healthcare facilities.

It is a further object of the present invention to provide a method and apparatus for sanitizing door handles that eliminates the unsightly appearance of a device being mounted on the outside of the door.

It is a further object of the present invention to provide a method and apparatus for sanitizing door handles that sanitizes all surfaces of the door handle during each application through the use of adjustable spray nozzles.

It is another object of the present invention to provide a method and apparatus for sanitizing door handles that includes either electronic or mechanical activation devices.

SUMMARY OF THE INVENTION

The present invention is directed to a door handle sanitizing cassette that is installed within an internal cavity formed within a door. The inventive cassette contains all the apparatus necessary for completely sanitizing the door handles with a sanitizing liquid before it is installed in the door, making installation quick, easy and cost effective. The cassette is designed to be compatible with all doors used within a health care facility and other public buildings. The cassette can be operated by electrical or mechanical power sources and an internal reservoir containing the sanitizing liquid can be a refillable container, a disposable container or a disposable container under pressure (eg. Aerosol can).

DETAILED DESCRIPTION

The present invention is directed to a cassette type door handle sanitizing system that is constructed of a durable and attractive material including, but not limited to, stainless steel or high performing plastic and/or stainless steel coated with high performance coating. The inventive cassette type system can be custom designed to accept all door handles/systems including, but not limited to, keyed, pass through, mechanical lock set, push/pull handles, panic bars, handicap push/pull mechanical door activators etc.

The cassette is designed to fit within an internal cavity custom formed within the door, with the cassette housing the mechanism to spray a sanitizing liquid on the door handle and the reservoir for the sanitizing liquid. The cassette will also contain the necessary equipment to spray the door handles at desire predetermined intervals and/or when the door is opened and closed as described below.

Figure 1:
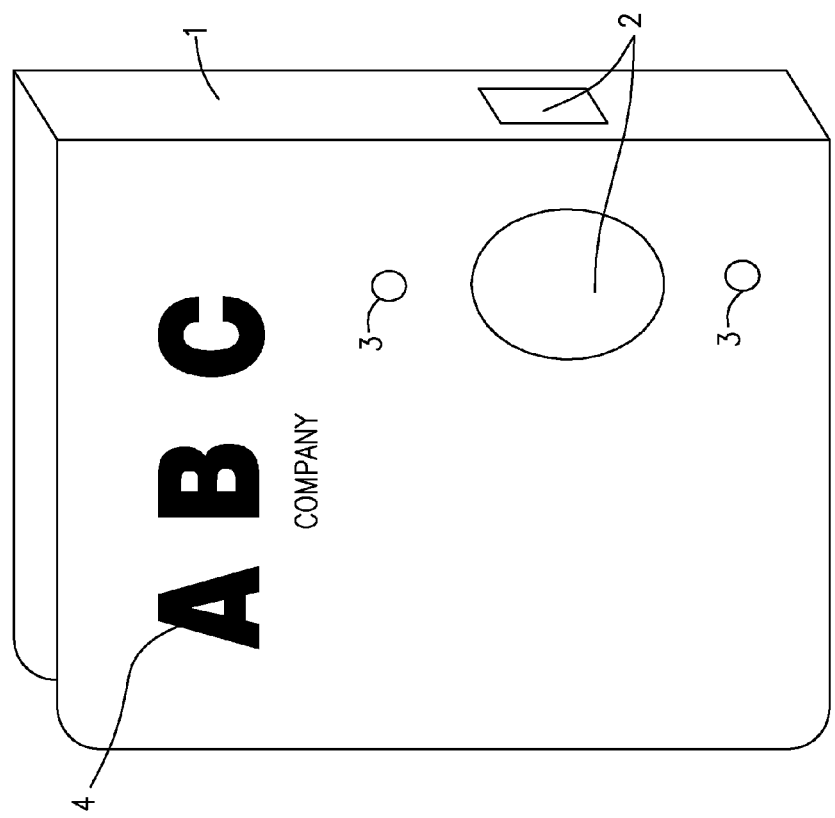
FIG. 1 is an exterior view of the inventive cassette before installation.
Figure 2:
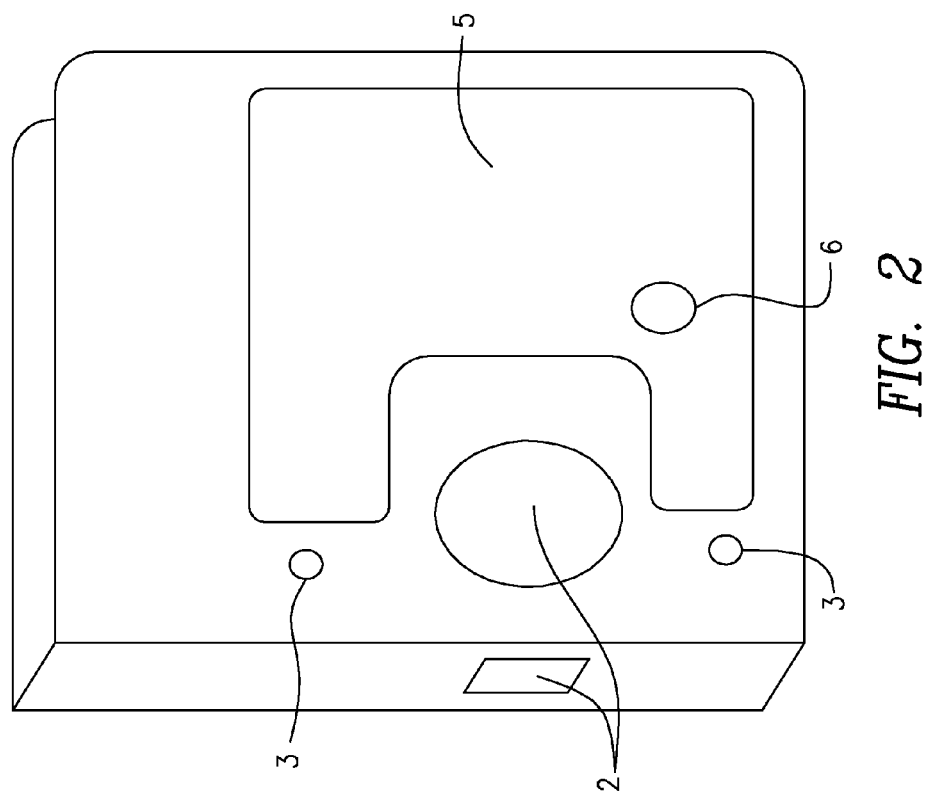
FIG. 2 is an interior view of the inventive cassette before installation.

Referring now to FIG. 1 there is shown an exterior side view of the cassette 1 of the present invention before installation in a door. The basic cassette contains standard or customized lockset holes at 2, holes for the spray nozzles at 3 and an area for company advertising at 4 which could include an electronic display or television monitor. FIG. 2 shows the interior side view of the basic cassette which further includes an access door 5 and a lockset hole 6 to secure a locking mechanism for the access door.

Figure 3:
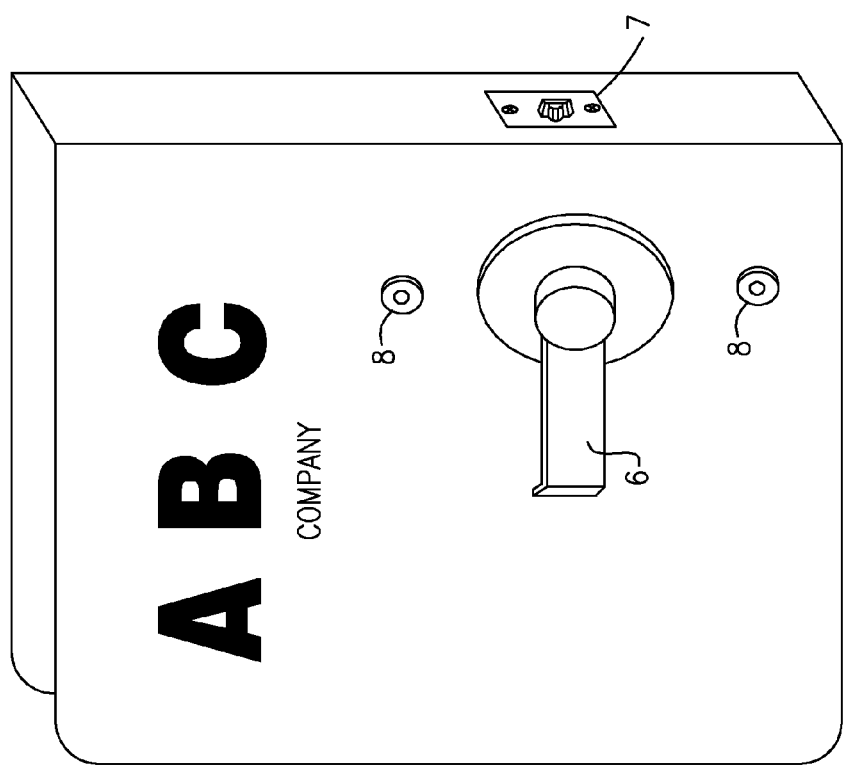
FIG. 3 is an exterior view of the inventive cassette with the door hardware installed.
Figure 4:
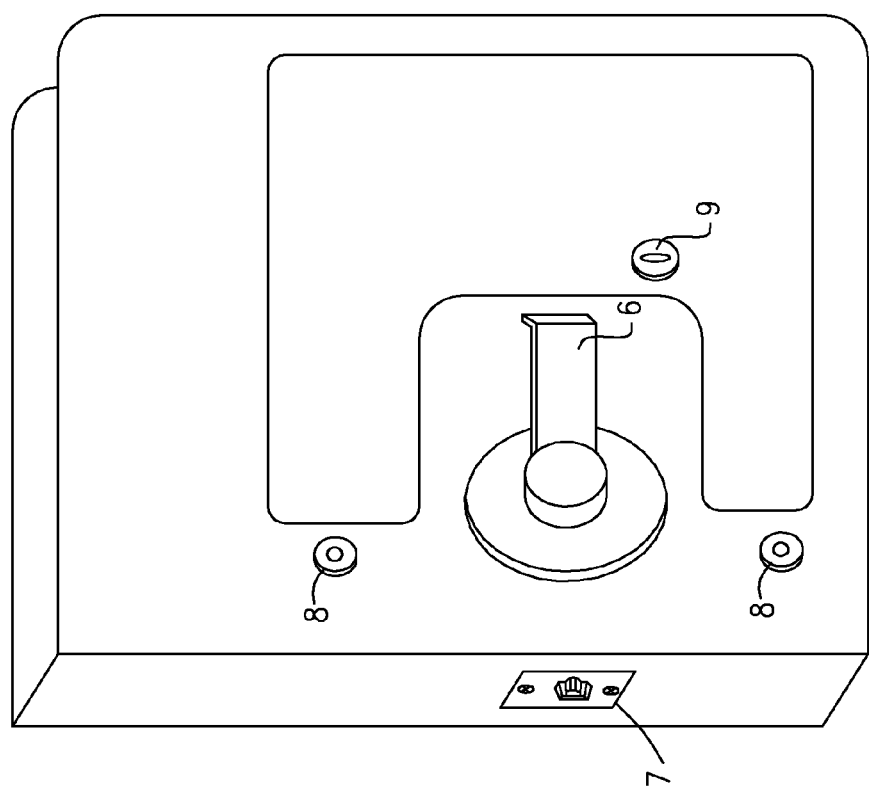
FIG. 4 is an interior view of the inventive cassette with the door hardware installed.

FIG. 3 shows the exterior view of the cassette with spray nozzles installed at 8 lockset hardware installed at 7 and a door handle at 6, while FIG. 4 shows the interior view of the cassette with installed hardware including a lock for the access door at 9.

FIGS. 3 and 4 illustrate the cassette just prior to installation in a custom formed cavity within a door. At this point the cassette would include all necessary door hardware and the internal mechanisms necessary for operation. The internal mechanism (not shown) will include in a first embodiment, an electrical battery powered pump to generate pressure or create a vacuum to deliver the sanitizing liquid, through internal plumbing tubes (not shown) to the spray nozzles. The spray nozzles are adjustable so the entire door handle is sprayed and may, if required, have an internal valve that will prevent undesired discharge of the sanitizing liquid when not in use but under pressure in anticipation of the next spray cycle.

The sanitizing liquid can be stored in a custom designed and permanent refillable reservoir. Alternatively the reservoir can be designed as a disposable cartridge, either under pressure from the installed pump or a pressurized aerosol can. Use of an aerosol can would eliminate the need for a pump and the power supply to operate the pump. The cassette can also include a timing mechanism (not shown) which can be either of electronic or mechanical design for initiating a spray cycle at specific intervals. In addition, the cassette will include a motion sensor to initiate the spray cycle each time the door is opened or closed. The motion sensor can include, but is not limited to, a pendulum sensor, a mercury switch, a door-to-door frame contact switch etc. In a preferred mode of operation the spraying cycle would be initiated by the motion sensor each time the door was opened or closed and also at predetermined intervals in response to the timing mechanisms when the door remained either open or closed for an extended interval.

In an alternative embodiment the spray cycle could be initiated by mechanical activation. This would include a plunger type pump connected to the spray nozzles tubing. The plunger for the pump can be installed at the door lock side where closing/opening would compress, push or pull the plunger to operate the pump. The plunger could also be installed at the hinge side to operate the pump when the door is opened or closed.

Figure 5:
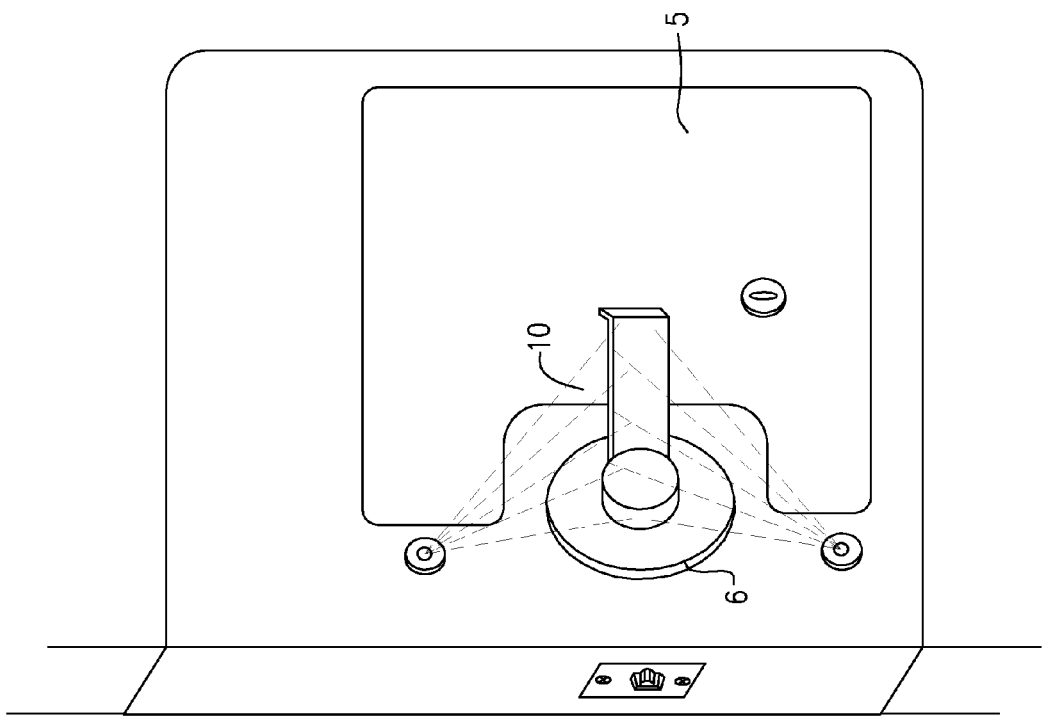
FIG. 5 is an interior view of the inventive cassette when installed in a door
Figure 6:
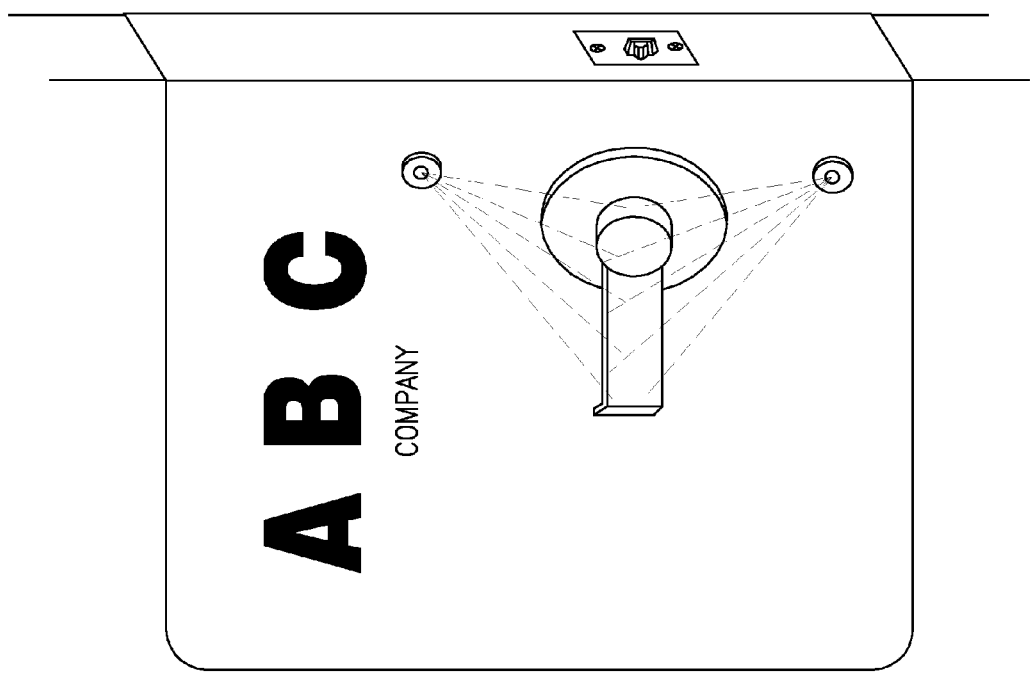
FIG. 6 illustrates the spray nozzles in operation.
Figure 7:
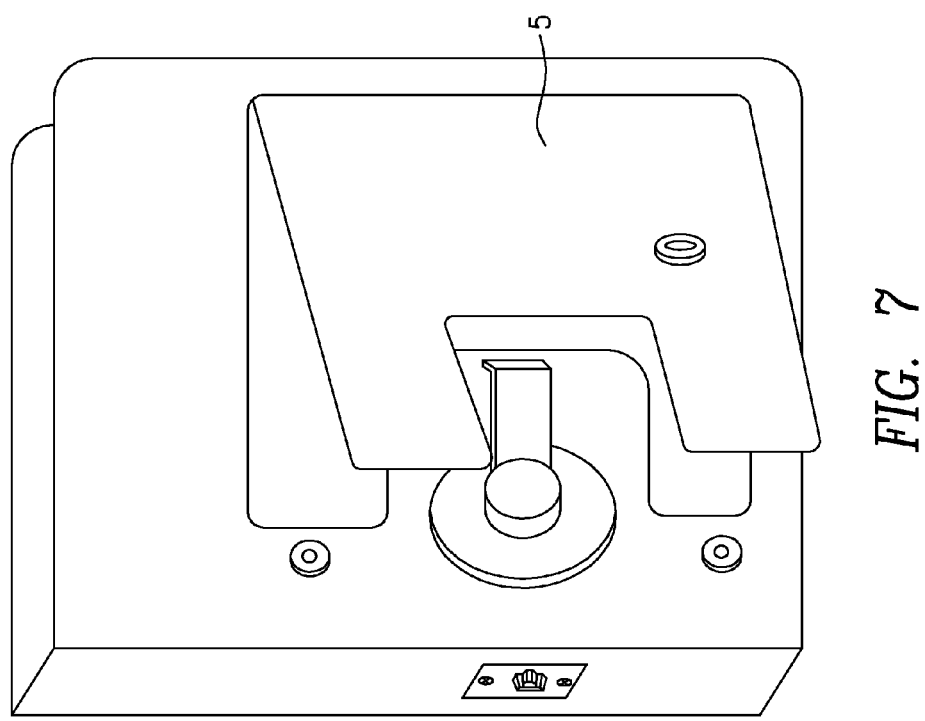
FIG. 7 illustrates the operation of an access door for maintenance purposes.

Referring now to FIG. 5 there is shown an interior side view of the door sanitizing cassette as installed in a custom cavity formed inside of a door. FIGS. 5 and 6 show the spray nozzles in operation at 10 which demonstrates that all surfaces of the door handles 6 are completely covered with sanitizing liquid. FIG. 7 illustrates the operation of access door 5 which is used to provide access for maintaining the spray mechanism described above and replenish the sanitizing liquid reservoir, either by refilling or by replacing the aerosol can itself.

While the invention has been described with reference to several embodiments thereof, the invention is more broadly defined and limited only by the claims appended hereto and their legal equivalents.

The invention claimed is:

1. A combined door and door handle hardware system comprising:
   a door having an internal cavity at a handle location;
   a body having a thickness of the door, the body having a first surface and an opposing second surface, the body attachable within the internal cavity formed in the door such that the body fills the internal cavity whereby the first surface is planar to a front surface of the door and the second surface is planar to a back surface of the door;
   a first hole formed in a first predetermined portion of the body for accommodating a handle;
   a second hole formed in a second predetermined portion of the body for accommodating lockset hardware;
   a third hole formed in a third predetermined portion of the body for accommodating a spray nozzle, the third hole located above the first hole;
   a fourth hole formed in a fourth predetermined portion of the body for accommodating a spray nozzle, the fourth hole located below the first hole;
   spray nozzles installed in each of the third hole and the fourth hole; and
   a reservoir within the body for storing said sanitizing liquid, said reservoir connected to said spray nozzles.

2. The combined door and door handle hardware system of claim 1, further comprising a battery powered pump to pump said sanitizing liquid from said reservoir to said spray nozzles.

3. The combined door and door handle hardware system of claim 1, further comprising a mechanically powered pump to pump said sanitizing liquid from said reservoir to said spray nozzles.

4. The combined door and door handle hardware system of claim 1, wherein said reservoir is a refillable container.

5. The combined door and door handle hardware system of claim 1, wherein said reservoir is an aerosol container.

6. The combined door and door handle hardware system of claim 1, further comprising a timing device for activating said spray nozzles at predetermined intervals.

7. The combined door and door handle hardware system of claim 1, there is further included a motion detector to detect when said door is opened or closed and to activate said spray nozzles in response thereto.

8. A combined door and door handle hardware system comprising:
   a door having an internal cavity at a handle location;
   a body having a thickness of the door, the body having a first surface and an opposing second surface, the body attachable within the internal cavity formed in the door such that the body fills the internal cavity whereby the first surface is planar to a front surface of the door and the second surface is planar to a back surface of the door;
   a first hole formed in a first predetermined portion of the body for accommodating a handle;
   a second hole formed in a second predetermined portion of the body for accommodating lockset hardware;
   a third hole formed in a third predetermined portion of the body; and
   a spray nozzle installed in the third hole;
   a reservoir within the body for storing said sanitizing liquid, said reservoir connected to said spray nozzle.

9. The combined door and door handle hardware system of claim 8, wherein said reservoir is a refillable container.

10. The combined door and door handle hardware system of claim 8, wherein said reservoir is an aerosol container.

11. The combined door and door handle hardware system of claim 8, further comprising a timing device for activating said spray nozzle at predetermined intervals.

12. The combined door and door handle hardware system of claim 8, wherein there is further included a motion detector to detect when said door is opened or closed and to activate said spray nozzle in response thereto.

* * * * *